(12) United States Patent
Leeflang et al.

(10) Patent No.: US 10,426,927 B2
(45) Date of Patent: Oct. 1, 2019

(54) TELESCOPING CATHETERS AND METHODS FOR USE

(71) Applicant: CLPH, LLC, Palo Alto, CA (US)

(72) Inventors: Stephen Arie Leeflang, Sunnyvale, CA (US); Christian S. Eversull, Palo Alto, CA (US)

(73) Assignee: CLPH, LLC, Palo Alto, CA (US)

( * ) Notice: Subject to any disclaimer, the term of this patent is extended or adjusted under 35 U.S.C. 154(b) by 333 days.

(21) Appl. No.: 15/172,148

(22) Filed: Jun. 2, 2016

(65) Prior Publication Data

US 2016/0367236 A1    Dec. 22, 2016

Related U.S. Application Data

(60) Provisional application No. 62/169,619, filed on Jun. 2, 2015.

(51) Int. Cl.
| | |
|---|---|
| *A61F 11/00* | (2006.01) |
| *A61M 25/01* | (2006.01) |
| *A61B 34/00* | (2016.01) |
| *A61B 18/14* | (2006.01) |
| *A61M 25/06* | (2006.01) |
| *A61B 17/00* | (2006.01) |
| *A61M 25/00* | (2006.01) |

(52) U.S. Cl.
CPC ..... *A61M 25/0127* (2013.01); *A61B 18/1492* (2013.01); *A61B 34/73* (2016.02); *A61M 25/0662* (2013.01); *A61B 2017/00305* (2013.01); *A61B 2017/00318* (2013.01); *A61B 2017/00876* (2013.01); *A61B 2017/00991* (2013.01); *A61B 2018/1475* (2013.01); *A61M 2025/0006* (2013.01); *A61M 2025/0175* (2013.01); *A61M 2025/0681* (2013.01); *A61M 2205/0272* (2013.01)

(58) Field of Classification Search
CPC .............. A61F 2/95; A61B 18/1492; A61B 2017/00305; A61B 2017/00318; A61B 2017/00876; A61B 2017/00991; A61M 25/0127; A61M 25/0662; A61M 2025/0175; A61M 2025/0681
See application file for complete search history.

(56) References Cited

U.S. PATENT DOCUMENTS

| | | | |
|---|---|---|---|
| 2014/0148889 A1* | 5/2014 | Deshmukh | A61F 2/962 623/1.11 |
| 2014/0243880 A1* | 8/2014 | Schotzko | A61F 2/013 606/200 |

* cited by examiner

*Primary Examiner* — Melanie R Tyson

(74) *Attorney, Agent, or Firm* — William A. English; Vista IP Law Group LLP

(57) ABSTRACT

Telescoping catheters are provided that include an outer tubular member and an inner member slidably received within a lumen of the outer member. The outer and inner members include cooperating magnetic elements on their distal ends. The magnetic elements may be mounted at locations to secure the inner member at a first axial position, e.g., a retracted position, using a magnetic attraction between the magnetic elements. The inner member may be moved axially from the first position by overcoming the magnetic attraction such that a predetermined axial force may disengage the magnetic elements to allow the first elongate member to directed from the first position to one or more other axial positions.

12 Claims, 2 Drawing Sheets

TELESCOPING CATHETERS AND METHODS FOR USE

RELATED APPLICATION DATA

The present application claims benefit of co-pending provisional application Ser. No. 62/169,619, filed Jun. 2, 2015, the entire disclosure of which is expressly incorporated by reference herein.

FIELD OF THE INVENTION

The present invention relates generally to catheters for performing medical procedures within a patient's body, and more particularly to catheters that include telescoping members that may be extended and retracted relative to one another and to systems and methods for using such catheters.

BACKGROUND

Telescopic catheters are commonly used to provide additional degrees of freedom to a catheter system for traversing complicated, tortuous, unsupported, and/or other challenging anatomy. While these generally work well, it can be cumbersome to keep track of the relative positions of the catheter elements, especially in systems where a highly flexible inner telescoping element is desired and/or relative positions of telescoping elements must remain finely indexed at the tip. These problems are exacerbated in conditions where a third or fourth inner telescoping element is desired. While position and locking mechanisms are common on the "back" end of these catheters, these elements are frequently insufficient to keep the "tips" of telescoping catheter elements aligned as desired. This is because the flexible, bendable nature of catheters causes path length changes in the catheters themselves, which render proximal end based alignment problematic/insufficient.

Therefore, apparatus and methods that facilitate use of such telescoping catheters would be useful.

SUMMARY

The present invention is directed to catheters for performing medical procedures within a patient's body. More particularly, the present invention is directed to catheters that include telescoping members that may be extended and retracted relative to one another and to systems and methods for using such catheters.

In accordance with one embodiment, an apparatus is provided for performing a procedure within a patient's body that includes two or more telescoping members that include magnetic tips on their distal ends. Magnet tipped telescoping elements on the members may provide distal indexing or locking of the telescoping members relative to each other in a desired position. The indexing or locking forces may be sufficient to keep the catheter in the desired position during typical manipulation, but may be "overcome" with minimal force when the relevant telescoping action is desired. This indexing or locking may be used/overcome repeatedly as needed. This is particularly useful in situations where one or more of the telescoping member are extremely flexible.

In an exemplary embodiment, for an apparatus including a pair of telescoping members, this may be accomplished by using two magnets or one magnet and one ferro-magnetic material (e.g., 416 stainless steel or other ferro-magnetic metal or alloy) component. In the case of the latter example, the inner member (may not be the most inner member depending on if there are additional telescoping members) indexing element may include the magnet and the outer member (may not be the most outer, depending on how if there are additional telescoping members) indexing element may include the ferro-magnetic component.

Conversely, the orientation may be switched, where the inner member indexing element is ferro-magnetic, and the outer member indexing element is magnetic.

Indexing or locking may occur inline (e.g., with one element inside another element) or at a face, e.g., with one element against another (e.g., an "end" cap like element locking against the face of the other locking element).

In accordance with another embodiment, an apparatus is provided for performing a medical procedure within a patient's body that includes a first elongate member comprising a first proximal portion, a first distal portion sized for introduction into a patient's body and including a first distal end, and a lumen extending between the first proximal portion and the first distal end; a second elongate member comprising a second proximal portion, a second distal portion slidably received within the lumen and including a second distal end, the second elongate member being movable relative to the first elongate member between a retracted position and a distal position where the second distal end extends distally from the first distal end; and cooperating magnetic elements on the first and second distal ends at locations to secure the second elongate member at the retracted position using a magnetic attraction between the magnetic elements. The magnetic attraction may be set such that a predetermined force may disengage the magnetic elements to allow the second elongate member to be directed from the retracted position towards the extended position.

In accordance with yet another embodiment, a method is provided for performing a procedure within a patient's body that includes providing a telescoping device including an outer member defining a lumen and an inner member slidably received within the lumen; introducing a distal portion of the outer member into the patient's body with a distal portion of the inner member disposed adjacent the outer member distal portion at a first position, the inner and outer members comprising cooperating magnetic elements securing the inner member distal portion at the first position; directing the inner member axially relative to the outer member with sufficient force to overcome a magnetic attraction of the magnetic elements; and directing the inner member axially relative to the outer member until the inner member returns to the first position, whereupon the magnetic elements automatically secure the inner member at the first position.

In accordance with still another embodiment, a method is provided for performing a procedure within a patient's body that includes introducing a distal portion of an outer member into the patient's body; with the outer member distal portion introduced into the patient's body, introducing a distal portion of an inner member into a lumen of the outer member until cooperating magnetic elements on the outer and inner members are aligned to secure the inner member distal portion at a first position; directing the inner member axially relative to the outer member with sufficient force to overcome a magnetic attraction of the magnetic elements and advance a distal end of the inner member distally from the outer member; and directing the inner member axially relative to the outer member until the inner member returns to the first position, whereupon the magnetic elements automatically secure the inner member at the first position.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION OF THE EXEMPLARY EMBODIMENTS

Figure 1:
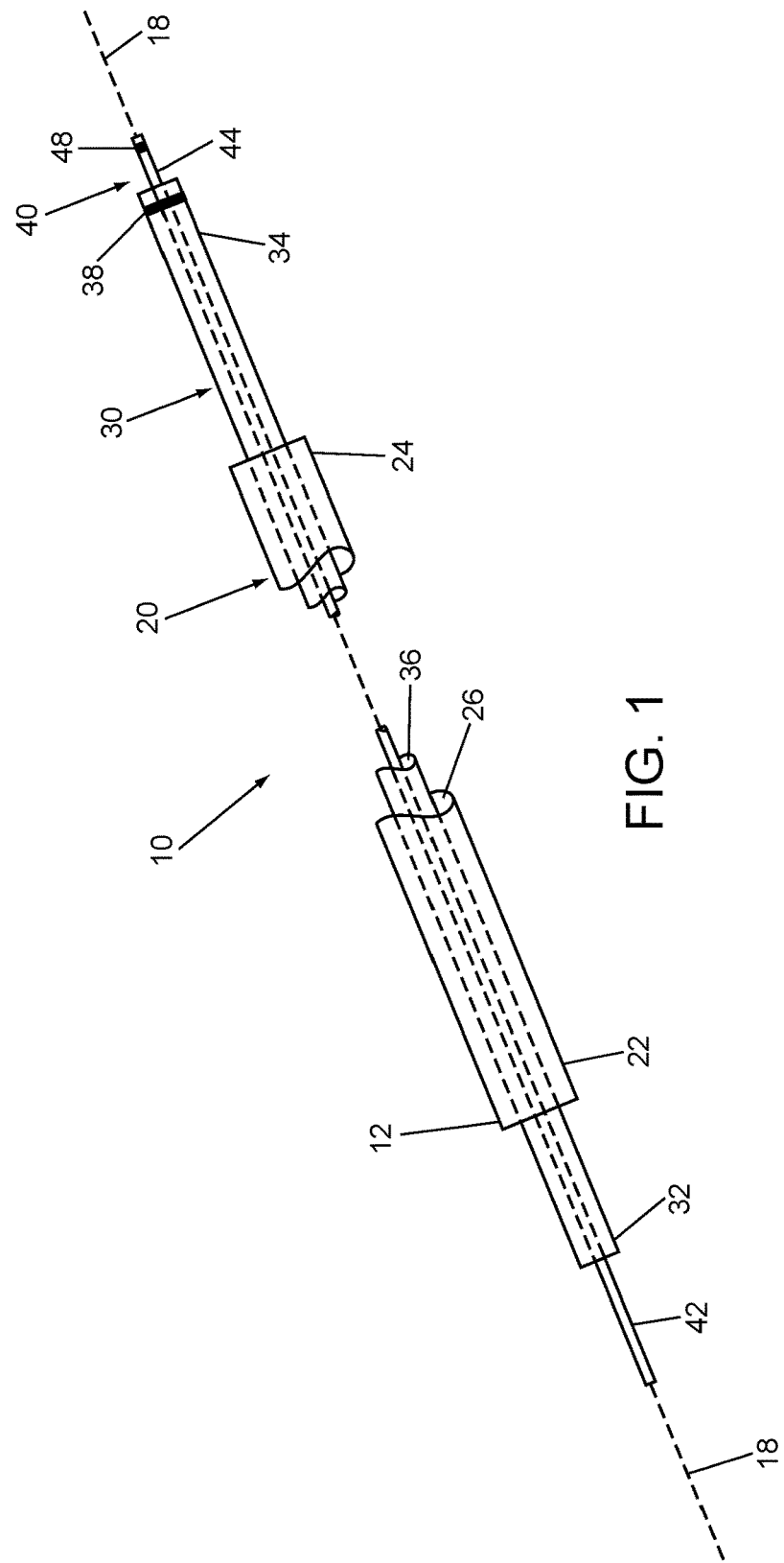
FIG. 1 is a side view of an exemplary embodiment of a telescoping catheter including magnetic features to selectively allow extending or retracting and indexing or locking of first and second catheter members relative to one another.
Figure 2A:
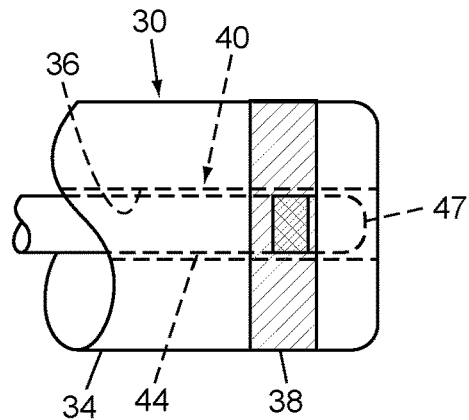
FIGS. 2A and 2B are details of distal ends of the first and second catheter members of FIG. 1 with the second member retracted and extended relative to the first member, respectively.
Figure 2B:
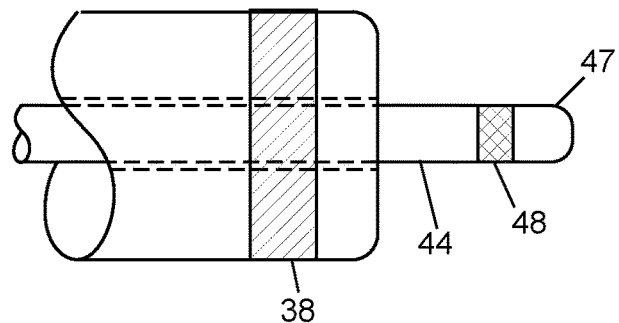

Turning to the drawings, FIGS. 1-2B show an exemplary embodiment of a telescoping catheter apparatus 10 for performing a medical procedure within a patient's body, e.g., for accessing a region within or adjacent a body lumen, that includes three telescoping catheter members 20, 30, 40. At least two of the members (e.g., intermediate member 30 and inner member 40, as shown) include cooperating magnetic elements 38, 48 configured to secure the members relative to one another at one or more positions, e.g., using a magnetic attraction between the magnetic elements. The magnetic attraction between the magnetic elements may be overcome such that a predetermined force may disengage the magnetic elements to allow the members 30, 40 to move relative to one another. Yet, the magnetic elements may bias the members 30, 40 to lock or otherwise index relative to one another when the magnetic elements are aligned, as described elsewhere herein.

Generally, as shown in FIG. 1, the outer member 20 is an elongate tubular member including a proximal portion or end 22, a distal portion or end 24 sized for introduction into a patient's body, and one or more lumens 28 extending between the proximal and distal ends 22, 24, e.g., generally defining a longitudinal axis 18 of the catheter 10. In the exemplary embodiment shown, the outer member 20 includes a primary or outer lumen 18a that slidably receives the other catheter members 30, 40. Optionally, the outer member 20 may include additional lumens, e.g., one or more steering element lumens for receiving a pull wire (not shown), e.g., if the distal end 24 of the outer member 20 is steerable and/or otherwise deflectable.

Similarly, the intermediate member 30 is an elongate tubular member including a proximal portion or end 32, a distal portion or end 34 sized to be slidable within the primary lumen 26, and an intermediate lumen 36 extending between the proximal and distal ends 32, 34. Also similarly, the inner member 40 includes a proximal portion or end 42 and a distal portion end or end 44 sized to be slidable within the intermediate lumen 36.

Optionally, the intermediate member 30 may include one or more additional lumens (not shown), e.g., a steering element lumen for receiving a pull wires (not shown), e.g., if the distal end 34 of the intermediate member 30 is steerable and/or otherwise deflectable. Similarly, the inner member 40 may optionally include one or more lumens (not shown), e.g., an infusion or delivery lumen for delivering fluids or other instruments from the inner member distal end 44, as described elsewhere herein.

Optionally, any of the distal ends 24, 34, 44 may include one or more features to enhance visibility under ultrasound, MRI or other imaging modalities, e.g., by providing one or more radiopaque markers on and/or doping one or more regions of the distal ends 24, 34, 44, e.g. as known in the art.

The catheter members 20, 30, 40 may be substantially flexible, semi-rigid, and/or rigid along their lengths, and may be formed from a variety of materials, including plastic, metal, and/or composite materials, as is well known to those skilled in the art. For example, the distal ends 24, 34, 44 may be substantially flexible to facilitate advancement through tortuous anatomy, and/or the proximal ends 22, 32, 42 may be semi-rigid or rigid to enhance pushability and/or torqueability of the catheter 10 and/or the individual members without substantial risk of buckling or kinking. In an exemplary embodiment, the inner member distal end 44 may be more flexible the intermediate member distal end 34, e.g., such that the intermediate member 30 may be used to support the inner member 40 until it is desired to extend the inner member 40, as described elsewhere herein.

In an exemplary embodiment, the outer and intermediate members 20, 30 may include an inner liner (not shown), e.g., at least partially or entirely surrounding or otherwise defining the lumens 26, 36, e.g., to facilitate slidably receiving the next telescoping member therein. In addition or alternatively, the outer and intermediate members 20, 30 optionally may include a reinforcement layer surrounding the inner liner, and an outer jacket surrounding the reinforcement layer (all not shown for simplicity), each of which may extend at least partially between the proximal ends 22, 32 and distal ends 24, 34 of the members 20, 30. Optionally, the lumens 26, 36 may include a lubricious material or may be formed from one or more layers of thermoplastic or other polymeric material including one or more coatings on the inner surface having desired properties, e.g., a hydrophilic and/or lubricious coating, e.g., similar to the liners disclosed in U.S. Pat. Nos. 7,550,053 and 7,553,387, and U.S. Publication No. 2009/0126862, the disclosures of which are expressly incorporated by reference herein.

The inner member 40 may be a solid or hollow body, e.g., a catheter, needle, or other shaft extendable from the intermediate member 30. Optionally, the inner member distal end 44 may carry one or more diagnostic or treatment members, e.g., electrodes, sensors, balloons, and the like (not shown), as described elsewhere herein.

With particular reference to the embodiment shown in FIGS. 2A and 2B, the magnetic elements may include a first or outer magnetic element 38 on the distal end 34 of the intermediate member 30 that at least partially surrounds the intermediate lumen 36 and a second or inner magnetic element 48 on the distal end 44 of the inner member 40. The relative locations of the magnetic elements 38, 48 may be offset from distal tips 37, 47 of the members 30, 40 such that the magnetic elements secure the inner member 40 in a retracted position, e.g., with the inner member distal tip 37 disposed within the intermediate lumen 36, as shown in FIG. 2A, yet may be advanced from the retracted position such that the inner member distal tip 47 extends distally from the intermediate member distal end 34, as shown in FIG. 2B, by overcoming the magnetic attraction between the magnetic elements 38, 48.

In an alternative embodiment, the inner magnetic element 48 may be offset from the inner member distal tip 47 by a predetermined distance such that a predetermined length of the inner member 40 extends from the intermediate member 30 when the magnetic elements 38, 48 are aligned. In this alternative, the inner member 40 may be retracted further from the retracted position, if desired, e.g., to retract the inner member 40 further (or entirely) into the intermediate lumen 36, or the retracted position may be the proximal-most position of the inner member 40.

In the embodiment shown, the outer magnetic element 38 has a shape that at least partially surrounds the lumen 36 at an axial location offset proximally from the intermediate member distal tip 37. For example, the outer magnetic element 38 may be a single annular member or may be formed from a plurality of elements spaced around the intermediate lumen 36 at the axial location, e.g., defining an interior region surrounding the intermediate lumen 34 at the axial location. The outer magnetic element 38 may be embedded within the material of the intermediate member 40 or may be fixed around the outside of the intermediate member distal end 34 or to an inner surface of the intermediate lumen 36, e.g., by interference fit, bonding with adhesive, and the like.

The inner magnetic element 48 may be a solid or hollow member carried on the inner member distal end 44. For example, if the inner member 40 includes an inner lumen (not shown), the inner magnetic element 48 may be a single annular member or a plurality of elements spaced around the inner lumen. Similar to the outer magnetic element 38, the inner magnetic element 48 may be embedded within the material of the inner member 40 or may be fixed around the outside of the intermediate member distal end 34, e.g., by interference fit, bonding with adhesive, and the like.

In one embodiment, the magnetic elements 38, 48 may include a first magnet on the intermediate member distal end 34 and a second magnet on the inner member distal end configured to be attracted to the first magnet. In this embodiment, the magnetic are configured such that the resultant magnetic fields cause the inner magnet to be attracted to the outer magnet when aligned within the interior region of the outer magnet, thus holding the inner magnet within the interior region and thereby securing the inner member 40 axially relative to the intermediate member 30.

In another embodiment, one of the magnetic elements 38, 48 may be a magnet and the other may be formed from ferro-magnetic material (e.g. 416 stainless steel or other ferro-magnetic metal or alloy). In this embodiment, the maximum magnetic attraction will occur when magnetic elements 38, 48 are aligned with the inner element 48 within the interior region of the outer element 38, thus again holding the inner element 48 within the interior region of the outer element 38 and thereby securing the inner member 40 axially relative to the outer member 30.

During use, with the magnetic elements 38, 48 aligned, the inner member 40 may be secured relative to the intermediate member 30 such that the inner member 40 simply follows movement of the intermediate member 30. However, at any time, the inner member 40 may be directed axially, e.g., distally to extend the inner member distal end 44 from the intermediate member 30. For example, if the inner member 40 includes a beveled, sharpened, or other needle tip (not shown), it may be desirable to fully retract the tip 47 completely within the intermediate lumen 36 to prevent inadvertent puncturing, skiving, or other damage to the patient by the tip 47. Alternatively, the inner member 40 may carry other treatment or diagnostic elements (not shown) adjacent the distal tip 47 that are fully retracted within the intermediate lumen 36, as desired. In a further alternative, the inner member 40 may simply be a guide member that may be extended from and retracted into the intermediate member 30, e.g., similar to a guidewire.

Optionally, one or more of the members 20, 30, 40 may include a handle or other features (not shown) to facilitate manipulation of the apparatus 10 and/or individual members 20, 30, 40. For example, a handle or hub (not shown) may be provided on the inner member proximal end 42, e.g., to limit the distance that the inner member 40 may be introduced into the intermediate member 30, e.g., to limit the length of the inner member distal end 44 that may be deployed. Optionally, the inner member 40 may be removable from the intermediate lumen 36, e.g., by simply pulling on the inner member proximal end 42 (or a handle or hub thereon). In this option, the inner member 40 (or another elongate member) may be selectively introduced into the intermediate lumen 36 and advanced, e.g., until the magnetic elements 38, 48 are aligned, thereby securing the inner member 40 relative to the intermediate member 30.

Alternatively, the inner member 40 may be permanently received within the intermediate lumen 36, e.g., by providing one or more stops (not shown) on the intermediate and/or inner members 30, 40 that limit proximal movement of the inner member 40. Similarly, the intermediate member 30 may be removable from or permanently received in the outer lumen 26.

In an exemplary embodiment, during use, with reference to FIGS. 2A and 2B, the apparatus 10 may be provided (or prepared outside the patient's body before a procedure) with the inner member 40 in the retracted position shown in FIG. 2A. The apparatus 10 may be introduced into a patient's body using conventional methods, e.g., from a percutaneous entry site into the patient's vasculature (not shown) into a target body lumen. In one embodiment, the outer member 20 may be a guide catheter or access sheath, which may be introduced initially into the patient's body, whereupon the intermediate and inner members 30, 40 may be introduced through the outer member 20 together, e.g., with the inner member 40 secured in the retracted position. In an alternative embodiment, the outer and intermediate members 20, 30 may include cooperating magnetic elements (not shown) such that the intermediate member 30 may be secured relative to the outer member 20, whereupon all three members 20, 30, 40 may be introduced simultaneously.

At any time, the magnetic attraction of the magnetic elements 38, 48 may be overcome by directing the inner member 40 distally relative to the intermediate member 30. For example, as shown in FIG. 1, the proximal end 42 of the inner member 40 may extend from the proximal end 32 of the intermediate member 30, which may extend from the proximal end 22 of the outer member 20. In this embodiment, the inner member 40 may be advanced from the retracted position simply by directing the inner member proximal end 42 distally relative to the intermediate member proximal end 32 (e.g., by advancing the inner member 40 or retracting the intermediate member 30). Given the magnetic attraction of the magnetic elements 38, 48, an initial resistance to movement must be overcome, whereupon the inner member 40 may be advanced freely relative to the intermediate member 30.

Optionally, the inner member 40 may include one or more additional magnetic elements (not shown), e.g., spaced apart proximally from the inner magnetic element 48. For example, a second inner magnetic element (not shown) may be spaced apart a predetermined distance proximally from the inner magnetic element 48 such that the second element becomes aligned with the outer magnetic element 38, thereby indexing or securing the inner member 40 with a corresponding predetermined length of the inner member distal end 44 extended from the intermediate member 30. Any desired number of additional inner magnetic elements may be provided, as desired, to bias the inner member 40 to desired positions, yet allowing further advancement of the inner member 40 simply by overcoming the magnetic attraction. Alternatively, one or more additional magnetic elements (not shown) may be provided on the intermediate member 30 proximal to the outer magnetic element 38 in addition or instead of providing multiple magnetic elements on the inner member 40. It will be appreciated that any desired number of magnetic elements may be provided to lock or index the inner member 40 at a plurality of axial positions relative to the intermediate member 30, yet allow the inner member 40 to be moved axially by overcoming the magnetic attraction of the aligned elements.

Alternatively, the apparatus 10 may include a handle (not shown) on the proximal end 12 that is coupled to one of the outer member 10 and the intermediate member 20 that includes an actuator (also not shown) coupled to the proximal end of the inner member 40. For example, the actuator may include a slider that may be advanced distally from a proximal position (where the inner member distal end 44 is fully retracted into the intermediate lumen 36, as shown in FIG. 2A) to a distal position (where the inner member distal end 44 extends from the intermediate lumen 36, as shown in FIG. 2B). Thus, the slider may define the range of axial movement of the inner member 40, while the magnetic elements 38, 48 may secure the inner member 40 in the retracted position (or in one or more intermediate positions, if additional inner magnetic elements are provided). Similarly, if a handle is provided on the outer member 20, an actuator may be provided on the handle (not shown) for limiting axial movement of the intermediate member 30 relative to the outer member 20. Thus, it may be possible to have a handle including actuators to selectively advance or retract the intermediate member 30 (e.g., with the inner member 40 locked in the retracted position) relative to the outer member 20 and independently advance or retract the inner member relative to the intermediate member 30.

In an exemplary method, the inner member 40 may carry one or more electrodes or sensors (not shown), which may be exposed when the inner member 40 is advanced, e.g., to perform an ablation procedure, perform a diagnostic procedure, and the like. For example, the intermediate member 30 (with the inner member 40 secured in the retracted position) may be introduced into a desired region within the patient's body. Once positioned as desired, the inner member 40 may be advanced to disengage the magnetic elements 38, 40 and extend the inner member distal end 44 from the intermediate lumen 36. The inner member 40 may be manipulated as desired to perform a procedure, e.g., by placing one or more electrodes or sensors in contact with tissue structures and the like. Once the procedure is completed, the inner member 40 may be retracted back into the intermediate member 30 with the magnetic elements 38, 48 again securing the inner member 40 in the retracted position. Optionally, the apparatus 10 may be directed to another location and the inner member 40 again deployed to perform an additional procedure.

In another method, the inner member 40 may define a hollow needle structure, e.g., which may be extended from the intermediate member 30 within a target body lumen to deliver one or more agents. For example, the inner member 40 may be deployed to direct the distal tip 47 through a wall of the body lumen to access a tissue region and deliver the agent(s) therein. Once the agent(s) is delivered, the inner member 40 may be retracted back into the intermediate member 30 with the magnetic elements 38, 48 again securing the inner member 40 in the retracted position.

Alternatively, the inner member 40 may be deployed a desired distance from the intermediate member 30 and, optionally, locked at an extended position, e.g., using a second set of magnetic elements (not shown), such that a desired length of the inner member distal end 44 is exposed. The intermediate member 30 may be manipulated as desired, e.g., directed towards a tissue structure and advanced to introduce the exposed inner member distal end 44 into the tissue structure, e.g., to deliver one or more agents therein. In this alternative, a spring or other resilient structure (not shown) may be provided, e.g., on the intermediate member proximal end 32, that prevents a distal force applied to the intermediate member proximal end 32 from exceeding the force of the magnetic elements 38, 48, to prevent the inner member 40 from being disengaged from the extended position. Once the agent is delivered, the inner member 40 may be withdrawn into the intermediate member 30, e.g., to the retracted position, where the first set of magnetic elements may lock the inner member 40 with the distal tip fully retracted into the intermediate lumen 36.

In still another method, the apparatus 10 may be used as an access device to facilitate introducing the distal ends 34, 44 of the intermediate and/or inner members 30, 40 through a series of body lumens within a patient's body. For example, the distal end 44 of the inner member 40 may be biased to a predetermined shape, e.g., a curvilinear shape, such as a simple curve or a complicated curve. When positioned within a first body lumen, the distal end 44 of the inner member 40 may be extended from the intermediate member 30 to access another body lumen, such as a main vessel to access a branch vessel or within a heart chamber to access a vessel communicating with the chamber (not shown). Once the desired body lumen is accessed, the intermediate member 30 may be advanced over the inner member 40, e.g., until the magnetic elements 38, 48 reengage, whereupon the intermediate and inner members 30, 40 may be advanced together, as desired. This procedure may repeated as often as desired to access a target location, e.g., to perform a procedure, e.g., using one or more elements, such as electrodes, sensors, and the like (not shown) on one or both of the intermediate member and inner member distal ends 34, 44.

Optionally, in this embodiment (or others herein), the magnetic elements 38, 48 may allow the inner member 40 to rotate freely within the intermediate lumen 36. For example, the inner member 40 may be rotated to orient the inner member distal end 44 in a desired direction before advancing the inner member 40, e.g., such that the curvilinear inner member distal end 44 deploys in a desired radial direction as it exits the intermediate lumen 34. Thus, the inner member distal end 44 may be directed transversely away from the longitudinal axis 18 of the apparatus 10, e.g., if desired to access body lumens (or tissue structures) disposed laterally relative to the intermediate member distal end 34.

Figure 3A:
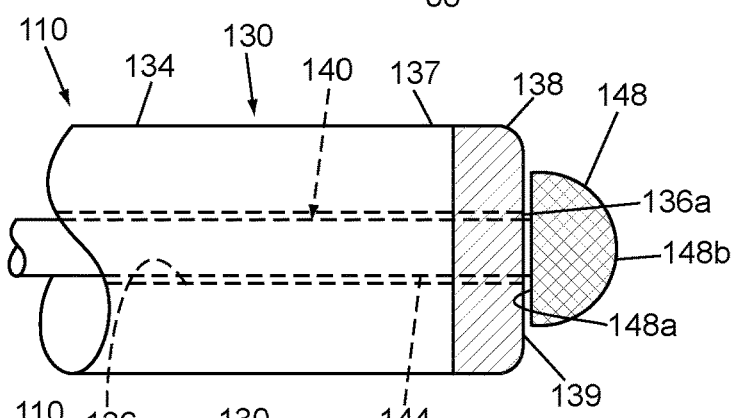
FIGS. 3A and 3B are details of distal ends of another embodiment of a telescoping catheter showing an inner catheter member retracted and extended relative to an outer catheter member, respectively.
Figure 3B:
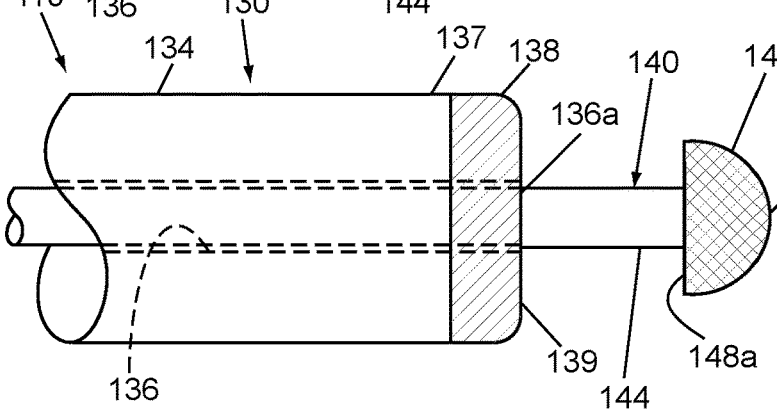

Turning to FIGS. 3A and 3B, another embodiment of an apparatus 110 is shown that includes an outer member 130 including a lumen 136 and inner member 140, e.g., generally similar to the intermediate and inner members 30, 40. Optionally, additional telescoping members (not shown) may be provided, as desired. As shown, the outer and inner members 130, 140 include cooperating magnetic elements 138, 148, e.g., a first or outer magnetic element 138 on a distal end or portion 134 of the outer member 130 and a second or inner magnetic element 148 on a distal end or portion 144 of the inner member 140.

Unlike the previous embodiment, the first magnetic element 138 is provided on a distal tip 137 of the outer member distal end 134, e.g., on or adjacent a distal face 139 of the distal tip 137, e.g., around an outlet 136a of the lumen 136. For example, the first magnetic element 138 may be mounted on the outer member distal tip 137, e.g., abutted onto the distal tip 137 and attached, e.g., by one or more of bonding with adhesive, using one or more cooperating connectors (not shown), and the like. Alternatively, the first magnetic element 138 may be at least partially embedded within the material of the outer member 130 immediately adjacent the distal face 139.

Also unlike the previous embodiment, the second magnetic element 148 is an enlarged member on the inner member 140 having a cross-section larger than the outlet 136a of the lumen 136. For example, as shown, the second magnetic element 148 may be an end cap carried on the inner member distal tip 147 having a substantially flat proximal surface 148a and a convex or rounded distal surface 148b. Thus, in this configuration, the inner member 140 may be directed to a retracted position where the proximal surface 148a of the second magnetic element contacts the distal face 139 of the outer member 130 and the distal surface 148b provides a rounded and/or otherwise atraumatic tip for the apparatus 110, as shown in FIG. 3A. In this position, magnetic attraction between the magnetic elements 138, 148 may secure the inner member 148 relative to the outer member 138. At any time, the inner member 140 may be advanced from the retracted position by overcoming the magnetic attraction to disengage the magnetic elements 138, 148 and expose a desired length of the inner member 140, as shown in FIG. 3B, similar to other embodiments herein.

Although the inner magnetic element 148 is shown defining a distal-most tip for the inner member 140 in FIGS. 3A and 3B, alternatively, the inner magnetic element may be offset proximally from the inner member distal tip 147. For example, the inner magnetic element may be a disk, an annular collar, one or more tabs, or any other structure (not shown) extending radially outwardly from the inner member distal end 144. Such an alternative inner magnetic element may be offset from the inner member distal tip 147 by a predetermined distance such that a predetermined length of the inner member 140 extends from the outer member 130 in the retracted position. When desired to deploy additional length of the inner member distal end 144, the inner member 140 may be advanced to disengage the magnetic elements 138, 148 and then freely moved to expose the desired length. In this alternative, the apparatus 110 may be used similar to the previous apparatus, although the inner member 140 may not be fully retracted into the outer member 130.

For example, a relatively short length of the inner member distal end 144 may extend from the intermediate member 130 in the retracted position, e.g., to provide a relatively small, atraumatic tip. When positioned within a first body lumen, the inner member 140 may be advanced to access a second body lumen. For example, the region of the inner member 140 within the lumen 136 immediately adjacent the outlet 136a may be biased to a curvilinear shape that may direct the inner member distal tip transversely as the inner member 140 is advanced, thereby facilitating accessing the second body lumen.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for performing a medical procedure within a patient's body, comprising:
    a first elongate member comprising a first proximal portion, a first distal portion sized for introduction into a patient's body and including a first distal end, and a lumen extending between the first proximal portion and the first distal end;
    a second elongate member comprising a second proximal portion, a second distal portion slidably received within the lumen and including a second distal end, the second elongate member being movable relative to the first elongate member between a retracted position and a distal position where the second distal end extends distally from the first distal end; and
    cooperating magnetic elements on the first and second distal ends at locations to secure the second elongate member at the retracted position using a magnetic attraction between the magnetic elements, the magnetic attraction being such that a predetermined force disengages the magnetic elements to allow the second elongate member to be directed from the retracted position towards the extended position,
    wherein the first distal end terminates at a first distal tip, and wherein the magnetic elements comprise a first magnetic element on the first distal tip at least partially surrounding an outlet of the lumen and a second magnetic element on the second distal end such that when the second distal end is directed to the retracted position, the second magnetic element abuts the first distal tip, and
    wherein the second elongate member terminates at a second distal tip, and wherein the second magnetic element comprises an enlarged member on the second distal tip having a cross-section larger than the outlet of the lumen such that the second magnetic element contacts the first distal tip surrounding the outlet.

2. The apparatus of claim 1, wherein the magnetic elements comprise a first magnet on the first distal end and a second magnet on the second distal end configured to be attracted to the first magnet.

3. The apparatus of claim 1, wherein the magnetic elements comprise a magnet on one of the first distal end and the second distal end and a ferro-magnetic element on the other of the first end and the second distal end configured to be attracted to the magnet.

4. The apparatus of claim 1, wherein the first magnetic element has an annular shape surrounding the outlet of the lumen.

5. An apparatus for performing a medical procedure within a patient's body, comprising:

a first elongate member comprising a first proximal portion, a first distal portion sized for introduction into a patient's body and including a first distal end, and a lumen extending between the first proximal portion and the first distal end;

a second elongate member comprising a second proximal portion, a second distal portion slidably received within the lumen and including a second distal end, the second elongate member being movable relative to the first elongate member between a retracted position and a distal position where the second distal end extends distally from the first distal en& and cooperating magnetic elements on the first and second distal ends at locations to secure the second elongate member at the retracted position using a magnetic attraction between the magnetic elements, the magnetic attraction being such that a predetermined force disengages the magnetic elements to allow the second elongate member to be directed from the retracted position towards the extended position, wherein the first distal end terminates at a first distal tip, and wherein the magnetic elements comprise a first magnetic element on the first distal tip at least partially surrounding an outlet of the lumen and a second magnetic element on the second distal end such that when the second distal end is directed to the retracted position, the second magnetic element abuts the first distal tip, and wherein the second elongate member terminates at a second distal tip, and wherein the second magnetic element extends radially outwardly from the second distal end proximal to the second distal tip, the second magnetic element having a cross-section larger than the outlet of the lumen such that the second magnetic element contacts the first distal tip surrounding the outlet.

6. The apparatus of claim 5, wherein a predetermined length of the second distal end extends distally from the first distal tip in the retracted position.

7. The apparatus of claim 5, wherein the first magnetic element has an annular shape surrounding the outlet of the lumen.

8. The apparatus of claim 5, wherein the magnetic elements comprise a first magnet on the first distal end and a second magnet on the second distal end configured to be attracted to the first magnet.

9. The apparatus of claim 5, wherein the magnetic elements comprise a magnet on one of the first distal end and the second distal end and a ferro-magnetic element on the other of the first end and the second distal end configured to be attracted to the magnet.

10. An apparatus for performing a medical procedure within a patient's body, comprising:
a first elongate member comprising a first proximal portion, a first distal portion sized for introduction into a patient's body and including a first distal end, a lumen extending between the first proximal portion and the first distal end, and a first magnetic element on a first distal tip of the first distal end at least partially surrounding an outlet of the lumen; and a second elongate member comprising a second proximal portion, a second distal portion slidably received within the lumen and including a second distal end, the second elongate member being movable relative to the first elongate member between a retracted position and a distal position where the second distal end extends distally from the first distal end, a second magnetic element on the second distal end;

wherein the first and second magnetic elements are configured to cooperate to secure the second elongate member at the retracted position using a magnetic attraction between the first and second magnetic elements such that the second magnetic element abuts the first distal tip in the retracted position, the magnetic attraction being such that a predetermined force disengages the first and second magnetic elements to allow the second elongate member to be directed from the retracted position towards the extended position, wherein the second elongate member terminates at a second distal tip, and wherein the second magnetic element comprises an enlarged member on the second distal tip having a cross-section larger than the outlet of the lumen such that the second magnetic element contacts the first distal tip surrounding the outlet.

11. The apparatus of claim 10, wherein a predetermined length of the second distal end extends distally from the first distal tip in the retracted position.

12. The apparatus of claim 10, wherein the first and second magnetic elements comprise a magnet on one of the first distal end and the second distal end and a ferro-magnetic element on the other of the first end and the second distal end configured to be attracted to the first magnet.

* * * * *